United States Patent [19]

Walther et al.

[11] Patent Number: 4,686,219
[45] Date of Patent: Aug. 11, 1987

[54] 11-(PIPERAZIN- OR HOMOPIPERAZIN-1-YL)-5H-IMIDAZO-(2,1-C)(1,4)BENZODIAZEPINES USEFUL AS ANTI-ALLERGICS

[75] Inventors: Gerhard Walther, Bingen; Claus Schneider, Ingelheim am Rhein; Karl-Heinz Weber; Armin Fügner, both of Gau-Algesheim, all of Fed. Rep. of Germany

[73] Assignee: Boehringer Ingelheim KG, Ingelheim am Rhein, Fed. Rep. of Germany

[21] Appl. No.: 827,849

[22] Filed: Feb. 7, 1986

Related U.S. Application Data

[63] Continuation of Ser. No. 645,009, Aug. 28, 1984, abandoned.

[30] Foreign Application Priority Data

Sep. 3, 1983 [DE] Fed. Rep. of Germany ....... 3331858

[51] Int. Cl.⁴ ..................... A61K 31/33; C07D 487/14
[52] U.S. Cl. .................................. 514/220; 540/498; 540/562; 548/337; 548/343
[58] Field of Search .......................... 540/562; 514/220

[56] References Cited

U.S. PATENT DOCUMENTS 4,460,508 7/1984 Vlattas ........................... 544/370
4,492,699 1/1985 Chakrabarti et al. ............ 544/366
4,495,101 1/1985 Klaubat et al. .................. 544/366

FOREIGN PATENT DOCUMENTS 137993 8/1984 European Pat. Off. .

OTHER PUBLICATIONS

Walther et al., Chem. Abst., 103-87912r, eq. DE 3331858.

Primary Examiner—Donald G. Daus
Assistant Examiner—Cecilia Shen
Attorney, Agent, or Firm—Hammond & Littell, Weissenberger & Dippert

[57] ABSTRACT

Compounds of the formula

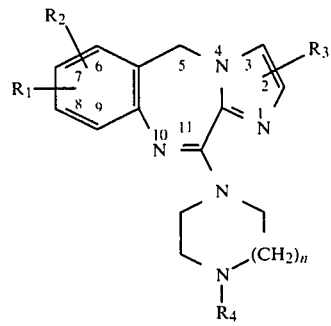

wherein
$R_1$ and $R_2$, which may be identical to or different from each other, are each hydrogen, fluorine, chlorine, bromine, trifluoromethyl, hydroxyl, nitro, amino, cyano, methylsulfonamido, alkyl of 1 to 4 carbon atoms, alkoxy of 1 to 3 carbon atoms, (alkyl of 1 to 3 carbon atoms)thio or (alkanoyl of 2 to 4 carbon atoms)amino;
$R_3$ is hydrogen, fluorine, chlorine, bromine or alkyl of 1 to 3 carbon atoms;
$R_4$ is hydrogen, alkyl of 1 to 4 carbon atoms, hydroxy(alkyl of 2 to 4 carbon atoms), (alkoxy of 1 to 2 carbon atoms)-(alkyl of 2 to 4 carbon atoms), alkenyl of 3 to 6 carbon atoms, alkynyl of 3 to 6 carbon atoms, cycloalkyl of 3 to 7 carbon atoms, (cycloalkyl of 3 to 7 carbon atoms)-(alkyl of 1 to 3 carbon atoms) or (unsubstituted or substituted phenyl)-(alkyl of 1 to 3 carbon atoms) where the substituent is fluorine, chlorine, bromine, methyl, methoxy, hydroxyl or trifluoromethyl; and
$n$ is 1 or 2;

and non-toxic, pharmacologically acceptable acid addition salts thereof. The compounds as well as their salts are useful as antiallergic.

7 Claims, No Drawings

11-(PIPERAZIN- OR HOMOPIPERAZIN-1-YL)-5H-IMIDAZO-(2,1-C)(1,4)BENZODIAZEPINES USEFUL AS ANTI-ALLERGICS

This is a continuation of Ser. No. 645,009, filed Aug. 28, 1984, now abandoned.

This invention relates to novel 11-[piperazin- or homopiperazin-1-yl]-5H-imidazo[2,1-c] [1,4]benzodiazepines and acid addition salts thereof, to methods of preparing these compounds, to pharmaceutical compositions containing them as active ingredients, and to a method of using them as antiallergics.

More particularly, the present invention relates to a novel class of compounds represented by the formula (I)

wherein

R$_1$ and R$_2$, which may be identical to or different from each other, are each hydrogen, fluorine, chlorine, bromine, trifluoromethyl, hydroxyl, nitro, amino, cyano, methylsulfonamido, alkyl of 1 to 4 carbon atoms, alkoxy of 1 to 3 carbon atoms, (alkyl of 1 to 3 carbon atoms)thio or (alkanoyl of 2 to 4 carbon atoms)amino;

R$_3$ is hydrogen, fluorine, chlorine, bromine or alkyl of 1 to 3 carbon atoms;

R$_4$ is hydrogen, alkyl of 1 to 4 carbon atoms, hydroxy(alkyl of 2 to 4 carbon atoms), (alkoxy of 1 to 2 carbon atoms)-(alkyl of 2 to 4 carbon atoms), alkenyl of 3 to 6 carbon atoms, alkynyl of 3 to 6 carbon atoms, cycloalkyl of 3 to 7 carbon atoms, (cycloalkyl of 3 to 7 carbon atoms)-(alkyl of 1 to 3 carbon atoms) or (unsubstituted or substituted phenyl)-(alkyl of 1 to 3 carbon atoms) where the substituent is fluorine, chlorine, bromine, methyl, methoxy, hydroxyl or trifluoromethyl; and n is 1 or 2;

and non-toxic, pharmacologically acceptable acid addition salts thereof.

A preferred subgenus thereunder is constituted by those compounds of the formula I where R$_1$ and R$_2$ are hydrogen, fluorine, chlorine or bromine in the 7- and 8-position;

R$_3$ is hydrogen; and

R$_4$ has the meanings previously defined;

and non-toxic, pharmacologically acceptable acid addition salts thereof.

An especially preferred subgenus is constituted by those compounds of the formula I where R$_1$ and R$_2$ are hydrogen, fluorine, chlorine or bromine in the 7- and 8-position;

R$_3$ is hydrogen; and

R$_4$ is hydrogen or methyl;

and non-toxic, pharmacologically acceptable acid addition salts thereof.

The compounds embraced by formula I may be prepared by the following methods:

Method A

By reacting a compound of the formula (II)

wherein R$_1$, R$_2$ and R$_3$ have the meanings previously defined, and X represents a groups which can be split off, with a piperazine of the formula (III)

wherein R$_4$ and n have the meanings previously defined. X may be an alkoxy or alkylmercapto group with 1–4 carbon atoms, a chlorine or bromine atom or =O or =S.

The reaction is preferably carried out in the presence of a tertiary amine, such as triethylamine, as an acid-binding agent when X=chlorine, bromine or iodine. However, it is also possible to use an excess of the amine of the formula III without any other solvent. When X represents an alkoxy or alkylmercapto group, the auxiliary base can be dispensed with. Suitable solvents include toluene or chlorobenzene. The reactions are preferably carried out at temperatures of from 100°–150° C., but can also be successfully carried out at lower temperatures with a correspondingly longer reaction time.

The reaction of compounds of the formula II in which X represents an oxygen atom with an amine of the formula III is carried out under the conditions described above in the presence of titanium tetrachloride. It has proved particularly advantageous to use anisole as the solvent or co-solvent, which forms a soluble complex with the titanium tetrachloride.

Compounds of the formula II where X is oxygen may be prepared in known manner by cyclizing aminoesters of the formula IV (R'=C$_{1-4}$ alkyl), for instance in the presence of dimethylsulfinyl sodium in a suitable solvent such as dimethylsulfoxide, or in the presence of an alkali metal alkoxide such as potassium tert. butoxide, in an inert solvent such as xylene. The compounds of the formula II where X is oxygen may also, however, be prepared in an acidic reaction solution, for example by heating a compound of the formula IV below in glacial acetic acid, optionally with the addition of catalytic quantities of p-toluenesulfonic acid. Another alternative for the preparation of compounds of the formula II where X is oxygen consists of cyclizing amino acids of the formula IV with a free carboxyl group, for example with cyclohexylcarbodiimide in a suitable solvent such as tetrahydrofuran.

The thioamides of the formula II (Y=S) are prepared by reacting the corresponding amides II (Y=O) with phosphorus pentasulfide in an anhydrous basic solvent such as pyridine, for example.

The compounds of the formula II where X=—SR, —OR or halogen may be obtained by reacting compounds of the formula II where X=O or S with conventional reagents. The compounds of the formula IV with a free carboxyl group may be obtained by hydrolyzing carboxylic acid esters of the formula IV (R'=alkyl) with sodium hydroxide in ethanol, for example.

Method B

By reacting a compound of the formula

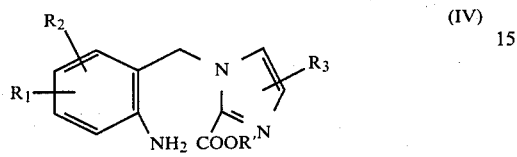

wherein $R_1$, $R_2$ and $R_3$ have the meanings previously defined, and R' is a lower alkyl, preferably methyl or ethyl, with a piperazine or homopiperazine of the formula III.

The reaction of a compound of the formula IV with a piperazine or homopiperazine of the formula III can also be successfully carried out in the presence of titanium tetrachloride under the reaction conditions described above under method A.

The amino esters of the formula IV used as starting materials may be prepared according to the following reaction sequence:

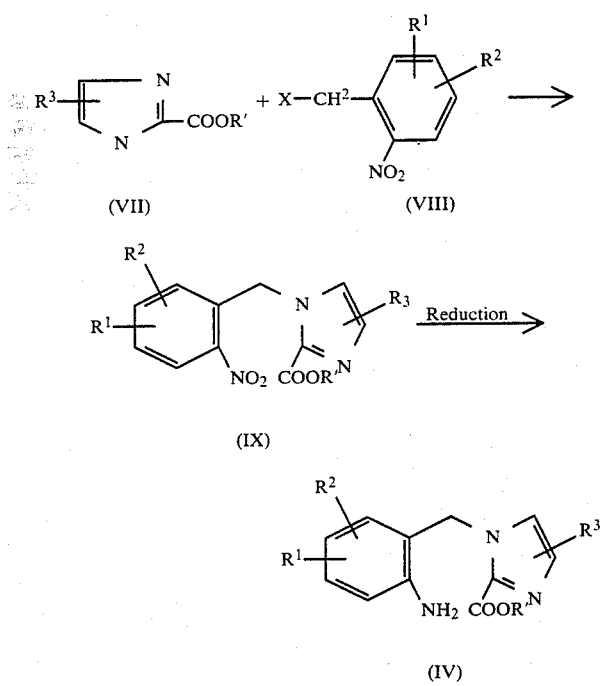

The compounds of the formula VII are known or may be prepared in analogy to methods described in the literature, such as K. L. Kirk, J. Org. Chem. 43/22, 4381–4383 (1978).

The alkylation of compounds of the formula VII is carried out in known manner by reaction with compounds of the formula VIII (X=for example, a halogen atom, preferably a chlorine or bromine atom or a tosyloxy or mesyloxy group). The reaction is preferably carried out in dimethylformamide in the presence of anhydrous potassium carbonate at a reaction temperature of 80°–120° C.

The nitro compounds of the formula IX may subsequently be converted into the corresponding amino compounds of the formula IV by reduction, for instance by catalytic hydrogenation in the presence of a suitable catalyst such as Raney nickel, with tin(II)chloride and hydrochloric acid in aqueous alcohol or ammonium polysulfide.

Method C

By reacting a compound of the formula

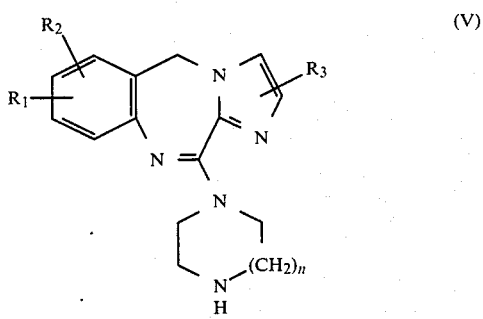

wherein $R_1$, $R_2$, $R_3$ and n have the meanings previously defined, with a compound of the formula $$R_4-Z \quad (VI)$$

wherein $R_4$ has the meanings previously defined with the exception of hydrogen, and Z is a group which can easily be split off, such as halogen, tosyloxy or mesyloxy.

The alkylation of compounds of the formula V with compounds of the formula VI is effected in a suitable inert solvent, for example in acetonitrile, an alcohol or a ketone at the reflux temperature of the reaction mixture, and optionally in the presence of an organic or inorganic base.

Depending on the starting compound used, one of the process variants described above may prove particularly favorable for the preparation of a particular end product.

The reaction products obtained by these various processes may be isolated by known laboratory methods. If desired, the crude products thus obtained may be purified by conventional methods, for example by column chromatography, before being crystallized in the form of bases or suitable salts.

The compounds embraced by formula I are basic and therefore form addition salts with inorganic or organic acids. Examples of non-toxic, pharmacologically acceptable acid addition salts are those formed with hydrohalic acids, sulfuric, phosphoric, nitric, cyclohexylsulfaminic, citric, tartaric, ascorbic, maleic, formic, salicylic acid, methane- or toluenesulfonic acid or the like.

The following examples illustrate the present invention and will enable others skilled in the art to understand it more completely. It should be understood, however, that the invention is not limited solely to the particular examples given below.

PREPARATION OF STARTING COMPOUNDS

EXAMPLE A

11-Methylthio-5H-imidazo[2,1-c] [1,4]benzodiazepine (a) Ethyl 1-(2-nitrobenzyl)-imidazole-2-carboxylate A mixture of 14 g (0.1 mol) of ethyl imidazol-2-carboxylate, 18.9 g (0.11 mol) of o-nitrobenzyl chloride, 13.8 g (0.1 mol) of anhydrous potassium carbonate and 100 ml of dimethylformamide was heated at 100° C. for 2 hours while stirring. Then, the solvent was substantially distilled off in vacuo, the residue was mixed with 100 ml of water and extracted with ethyl acetate. The organic phase was washed twice with water, dried over anhydrous sodium sulfate and concentrated by evaporation. The crystalline residue was suspended in ether, and the suspension was suction-filtered. 23.5 g (85.4% of theory) of ethyl 1-(2-nitrobenzyl)-imidazole-2-carboxylate, m.p. 107°–111° C., were obtained.

Analogously, the following compounds were prepared from the corresponding o-nitrobenzyl halides and ethyl imidazole-2-carboxylates:
Ethyl 1-(2-nitro-4-chloro-benzyl)-imidazole-2-carboxylate;
Ethyl 1-(2-nitro-5-methyl-benzyl)-imidazole-2-carboxylate, m.p. 105°–107° C. (ethyl acetate/gasoline);
Ethyl 1-(2-nitro-5-chloro-benzyl)-imidazole-2-carboxylate;
Ethyl 1-(2-nitro-5-methoxy-benzyl)-imidazole-2-carboxylate;
Ethyl 1-(2-nitro-4-fluoro-benzyl)-imidazole-2-carboxylate.

(b) Ethyl 1-(2-aminobenzyl)-imidazole-2-carboxylate 49.6 g (0.18 mol) of ethyl 1-(2-nitrobenzyl)-imidazole-2-carboxylate were hydrogenated in 500 ml of tetrahydrofuran at room temperature under a pressure of 5 bar in the presence of Raney nickel. After the theoretical quantity of hydrogen had been absorbed, the catalyst was suction-filtered off, and the filtrate was evaporated. 37.7 g (85.4% of theory) of ethyl 1-(2-aminobenzyl)-imidazol-2-carboxylate, m.p. 104°–106° C. (m.p. from toluene 105°–107° C.) were obtained.

The following amino compounds were prepared analogously from the corresponding nitro compounds.
Ethyl 1-(2-amino-4-chloro-benzyl)-imidazole-2-carboxylate;
Ethyl 1-(2-amino-5-methyl-benzyl)-imidazole-2-carboxylate, m.p. 94°–96° C. (toluene/gasoline);
Ethyl 1-(2-amino-5-chloro-benzyl)-imidazole-2-carboxylate;
Ethyl 1-(2-amino-5-methoxy-benzyl)-imidazole-2-carboxylate;
Ethyl 1-(2-amino-4-fluoro-benzyl)-imidazole-2-carboxylate.

(c) 10,11-Dihydro-5H-imidazo[2,1-c] [1,4]benzodiazepin-11-one (α) A solution of 10 g (0.04 mol) of ethyl 1-(2-aminobenzyl)-imidazole-2-carboxylate in 70 ml of glacial acetic acid was refluxed for 3 hours. After evaporation, the residue was dissolved in 40 ml of methanol, and the methanolic solution was mixed with ethereal hydrochloric acid until an acidic reaction was obtained. The crystals obtained were suction-filtered off, washed with ether and dried. 8.6 g (89.4% of theory) of 10,11-dihydro-5H-imidazo[2,1-c] [1,4]benzodiazepin-11-one hydrochloride were obtained, m.p. 315° C. (decomp.).

The following compounds were prepared analogously: 8-Chloro-10,11-dihydro-5H-imidazo[2,1-c] [1,4]benzodiazepin-11-one hydrochloride; 7-Methyl-10,11-dihydro-5H-imidazo[2,1-c] [1,4]-benzodiazepin-11-one hydrochloride, m.p. 314° C. decomp.); 7-Methoxy-10,11-dihydro-5H-imidazo[2,1-c] [1,4]benzodiazepin-11-one hydrochloride.

(β) A mixture of 500 mg of ethyl 1-(2-aminobenzyl)-imidazole-2-carboxylate, 80 mg of potassium tert.butoxide and 3 ml of dimethylformamide was heated at 150° C. for 15 minutes while stirring. Then, the solvent was distilled off in vacuo, and the residue was treated with a little water and cyclohexane. The crystals thus formed were suction-filtered off, washed with acetone and dissolved in methanol after drying. When the methanolic solution was acidified with ethereal hydrochloric acid, 285 mg (62.6% of theory) of 10,11-dihydro-5H-imidazo[2,1-c] [1,4]benzodiazepin-11-one hydrochloride, m.p. 312° C. (decomp.), were obtained.

(d) 10,11-Dihydro-5H-imidazo[2,1-c] [1,4]benzodiazepin-11-thione

A mixture of 2.35 g (0.01 mol) of 10,11-dihydro-5H-imidazo[2,1-c] [1,4]benzodiazepin-11-one hydrochloride, 0.89 g (0.004 mol) of phosphorus pentasulfide and 25 ml of absolute pyridine was refluxed for 4 hours while stirring. Then, the pyridine was evaporated, and the residue was treated with 25 ml of an aqueous 5% sodium carbonate solution and 1 ml of methanol.

After the mixture had been stirred for some time, crystallization gradually set in. The light brown crystals were suction-filtered off, washed with water and dried. Yield: 1.95 g (90.7% of theory); m.p. 222°–227° C. After being recrystallized from acetonitrile the compound melted at 227°–231° C.

The following compound was prepared analogously: 7-Methoxy-10,11-dihydro-5H-imidazo[2,1-c] [1,4]benzodiazepin-11-one.

(e) 11-Methylthio-5H-imidazo[2,1-c] [1,4]benzodiazepine

A solution of 1.1 g (0.048 mol) of sodium in 120 ml of ethanol was combined, while stirring, with 10.3 g (0.048 mol) of 10,11-dihydro-5H-imidazo[2,1-c] [1,4]benzodiazepin-11-thione. After one hour, 4.8 ml of methyl iodide were added at room temperature. A precipitate gradually formed. After 4 hours the suspension was stirred at room temperature, and then the solvent was distilled off in vacuo. The residue was taken up in chloroform, and extracted with a dilute aqueous potassium carbonate solution.

The organic phase was separated, dried over anhydrous sodium sulfate and evaporated in vacuo. The residue [10 g (91% of theory); m.p. 144°–150° C.] could be reacted further without any additional purification.

The following compound was prepared analogously: 7-Methoxy-11-methylthio-5H-imidazo[2,1-c] [1,4]benzodiazepine.

PREPARATION OF END PRODUCTS OF THE FORMULA I

EXAMPLE 1

11-[4-Methyl-piperazin(1)yl]-5H-imidazo[2,1-c] [1,4]-benzodiazepine by method A

A mixture of 5 g (0.22 mol) of 11-methylthio-5H-imidazo[2,1-c] [1,4]benzodiazepine (m.p. 144°–150° C.), 17.5 g (0.175 mol) of 1-methyl-piperazine, 10 drops of glacial acetic acid and 45 ml of xylene was refluxed for 24 hours. The reaction mixture was then evaporated in vacuo, and the residue was taken up in a mixture of chloroform and dilute aqueous potassium carbonate solution. The organic phase was separated, dried with anhydrous sodium sulfate, and the solvent was distilled off. The residue (5.3 g) was subsequently chromatographed on silica gel with methanol. The pure fractions were collected and evaporated. The resdue was recrystallized from toluene/gasoline. 2.5 g (40.8% of theory) of pure 11-[4-methyl-piperazin(1)yl]-5H-imidazo[2,1-c] [1,4]benzodiazepine were obtained (m.p. 121°–124° C.).

The following compounds were obtained analogously:
11-(1-Piperazinyl)-5H-imidazo[2,1-c] [1,4]benzodiazepine, m.p. 175°–177° C. (toluene), by reacting 11-methylthio-5H-imidazo-[2,1-c] [1,4]benzodiazepine with piperazine;
7-Methoxy-11[4-methyl-piperazin-(1)-yl]-5H-imidazo[2,1-c] [1,4]benzodiazepine by reacting 7-methoxy-11-methylthio-5H-imidazo-[2,1-c] [1,4]benzodiazepine with 1-methyl-piperazine.

EXAMPLE 2

11-[4-Methyl-piperazin-(1)-yl]-5H-imidazo[2,1-c] [1,4]benzodiazepine by method B A solution of 3 ml of titanium tetrachloride in 12 ml of anisole was slowly added dropwise, while stirring and in a nitrogen atmosphere, to a solution of 2.5 g (0.01 mol) of ethyl 1-(2-aminobenzyl)-imidazole-2-carboxylate in 12 ml of 1-methyl-piperazine and 50 ml of anisole. The reaction micture was refluxed for one hour. After cooling, the insoluble components were removed, and the solution thus obtained was extracted with an aqueous 40% potassium carbonate solution. The organic phase was washed with water and, after drying with anhydrous sodium sulfate, was evaporated in vacuo. The partly crystalline residue (4.2 g) was washed with gasoline and dried. The yield of pure 11-[4-methyl-piperazin-(1)-yl]-5H-imidazo[2,1-c] [1,4]benzodiazepine was 2.4 g (83.7% of theory); m.p. 123°–125° C.

The following compounds were prepared by the same method:
8-Chloro-11-[4-methyl-piperazin-(1)-yl]-5H-imidazo[2,1-c] [1,4]benzodiazepine; m.p. 177°–179° C. (ethyl acetate/gasoline).
8-Chloro-11-(1-piperazinyl)-5H-imidazo[2,1-c] [1,4]benzodiazepine; m.p. 120°–123° C. (ethyl acetate/gasoline).
7-Methyl-11-[4-methyl-piperazin-(1)-yl]-5H-imidazo[2,1-c] [1,4]benzodiazepine; m.p. 170°–172° C.
11-[4-Benzyl-piperazin-(1)-yl]-5H-imidazo[2,1-c] [1,4]benzodiazepine; m.p. 158°–159° C. (ethyl acetate/gasoline).
11-[4-Methyl-homopiperazin-(1)-yl]-5H-imidazo[2,1-c] [1,4]benzodiazepine.
7-Chloro-11-[4-methyl-piperazin-(1)-yl]-5H-imidazo[2,1-c] [1,4]benzodiazepine.
8-Fluoro-11-[4-methyl-piperazin-(1)-yl]-5H-imidazo[2,1-c] [1,4]benzodiazepine.
11-[4-Ethyl-piperazin-(1)-yl]-5H-imidazo[2,1-c] [1,4]benzodiazepine; m.p. 129°–130° C.

EXAMPLE 3

11-[4-Methyl-piperazin-(1)-yl]-5H-imidazo[2,1-c] [1,4]-benzodiazepine by method A A solution of 6.3 ml of titanium tetrachloride in 30 ml of anisole was added dropwise, while stirring and in a nitrogen atmosphere, to a suspension of 5 g (0.02 mol) of 10,11-dihydro-5H-imidazo [2,1-c] [1,4]benzodiazepin-11-one hydrochloride in 70 ml of anisole and 20 ml of 1-methyl-piperazine. The reaction mixture was reluxed for one hour and then cooled to about 60° C. After the insoluble matter had been removed, the cooled reaction solution was diluted with 50 ml of toluene and extracted with 40 ml of a saturated aqueous potassium carbonate solution. The organic phase was evaporated and after drying it over anhydrous sodium sulfate it was evaporated in vacuo. The crystalline residue was washed with gasoline. 4.7 g (78.7% of theory) of 11-[4-methyl-piperazin-(1)-yl]-5H-imidazo[2,1-c] [1,4]benzodiazepine, m.p. 121°–123° C., were obtained.

EXAMPLE 4

11-[4-Allyl-piperazin-(1)-yl]-5H-imidazo[2,1-c] [1,4]benzodiazepine by method C A solution of 2.9 g (0.011 mol) of 11-(1-piperazinyl)-5H-imidazo[2,1-c] [1,4]benzodiazepine in 50 ml of methanol was mixed with 1.5 g (0.011 mol) of anhydrous potassium carbonate and 1.44 g (0.012 mol) of allyl bromide. The reaction mixture was heated at 60° C. for one hour while stirring. Then, the solvent was distilled off, and the residue was taken up in a mixture of chloroform and water. After drying it over anhydrous sodium sulfate the organic phase was evaporated. The residue was purified by column chromatography (silica gel/methanol) and subsequent recrystallization with acetonitrile. 1.9 g (57% of theory) of 11-[4-allyl-piperazin-(1)-yl]-5H-imidazo[2,1-c] [1,4]benzodiazepine, m.p. 168°–170° C., were obtained.

The following compounds were prepared analogously:
8-Chloro-11-[4-(2-hydroxyethyl)-piperazin-(1)-yl]-5H-imidazo-[2,1-c] [1,4]benzodiazepine.
8-Chloro-11-[4-cyclopropylmethyl-piperazin-(1)-yl]-5H-imidazo-[2,1-c] [1,4]benzodiazepine.
8-Chloro-11-[4-propargyl-piperazin-(1)-yl]-5H-imidazo[2,1-c] [1,4]benzodiazepine.
11-[4-(3-Hydroxypropyl)-piperazin-(1)-yl]-5H-imidazo[2,1-c] [1,4]benzodiazepine.

The compounds of the present invention, that is, those embraced by formula I above and their non-toxic, pharmacologically acceptable acid addition salts, have useful pharmacodynamic properties. More particularly, they exhibit antiallergic activity in warm-blooded animals. Some of them also exhibit analgesic, antihistaminic or neuroleptic activities.

They are from 10 to more than 300 times more active than the known commercial products ketotifen and promethazin in the PCA test [Goose et al., Immunology 16, 749 (1969)]. Unlike the known commercial product Intal ®, they are also orally effective.

For pharmaceutical purposes the compounds of the present invention are administered to warm-blooded animals perorally, parenterally or rectally as active ingredients in customary pharmaceutical compositions, that is, compositions consisting essentially of an inert pharmaceutical carrier and an effective amount of the active ingredient. An effective amount of the compounds of the present invention is from 0.016 to 1.6 mgm/kg body weight, preferably 0.03 to 0.83 mgm/kg body weight.

Suitable forms of administration include, for example, tablets, capsules, suppositories, solutions, syrups, emulsions, aerosols and dispersible powders. Tablets may be produced, for example, by mixing the active substance or substances with known excipients such as inert diluents, for example calcium carbonate, calcium phosphate or lactose; disintegrants such as corn starch or alginic acid; binders such as starch or gelatin; lubricants such as magnesium stearate or talc; and/or release agents, such as carboxypolymethylene, carboxylmethylcellulose, cellulose acetate phthalate or polyvinyl acetate. The tablets may also consist of several layers.

Coated tablets may be produced by coating tablet cores, made in the same way as the tablets, with agents conventionally used for tablet coatings, such as collidone or shellack, gum arabic, talc, titanium dioxide or sugar. In order to obtain delayed release or avoid incompatibilities, the core may also consist of several layers. Similarly, The tablet shell may consist of several layers in order to obtain a delayed release, and the excipients mentioned above for the tablets may be used.

Syrups of the active ingredient or combinations of active ingredients of the invention may additionally contain a sweetener such as saccharin, cyclamate, glycerol or sugar and a flavor-improving agent, for instance a flavoring such as vanillin or orange extract. They may also contain suspension adjuvants or thickeners such as sodium carboxymethylcellulose, wetting agents, such as condensation products of fatty alcohols with ethylene oxide, or preservatives such as p-hydroxybenzoates.

Injection solutions are prepared in the usual way, for example by adding preservatives such as p-hydroxybenzoates or stabilizers such as alkali metal salts of ethylene diamine tetraacetic acid and the solutions are filled into injection vials or ampules.

Capsules containing one or more active substances or combinations of active ingredients may be prepared, for example, by mixing the active ingredients with inert carriers such as lactose or sorbitol, and encapsulating the mixture in gelatin capsules.

Suitable suppositories may be prepared, for example, by mixing with carriers provided for this purpose, such as neutral fats or polyethyleneglycol or the derivatives thereof.

The following examples illustrate a few pharmaceutical compositions comprising a compound of the present invention as an active ingredient and represent the best modes contemplated of using the invention. The parts are parts by weight unless otherwise specified.

EXAMPLE 5

Coated Tablets

The tablet core composition is compounded from the following ingredients:

| | |
|---|---|
| 11-[4-Methyl-piperazin-(1)-yl]-5H—imidazo[2,1-c][1,4]benzodiazepines | 50.0 parts |
| Lactose | 28.5 parts |
| Corn starch | 17.0 parts |
| Gelatin | 2.0 parts |
| Magnesium stearate | 0.5 parts |
| | 98.0 parts |

Preparation

A mixture of the active ingredient with the lactose and the corn starch is passed through a 1 mm-mesh screen with an aqueous 10% gelatin solution, then dried at 40° C. and passed through a screen again. The granulate thus obtained is mixed with the magnesium stearate and compressed into 98 mg-tablet cores. The cores are coated with a shell which is applied in the usual way by means of an aqueous suspension of sugar, titanium dioxide, talc and gum arabic. The finished coated tablets are polished with beeswax.

EXAMPLE 6

Tablets

The tablet composition is compounded from the following ingredients:

| | |
|---|---|
| 11-[4-Methyl-piperazin-(1)-yl]-5H—imidazo[2,1-c][1,4]benzodiazepine | 20.0 parts |
| Lactose | 55.0 parts |
| Corn starch | 38.0 parts |
| Soluble starch | 4.0 parts |
| Magnesium stearate | 1.0 parts |
| | 118.0 parts |

Preparation

The active ingredient and the magnesium stearate are mixed and granulated with an aqueous solution of the soluble starch, the granulate is dried and intimately mixed with the lactose and the corn starch. The composition is then compressed into tablets weighing 118 mg each. They each contain 20 mg of the active ingredient.

EXAMPLE 7

Suppositories

The suppository composition is compounded from the following ingredients:

| | |
|---|---|
| 11-[4-Methyl-piperazin-(1)-yl]-5H—imidazo[2,1-c][1,4]benzodiazepine | 5.0 parts |
| Suppository base (e.g. cocoa butter) | 1695.0 parts |
| | 1700.0 parts |

Preparation

The finely powdered active ingredient is stirred with the aid of an immersion homogenizer into the suppository base which has been melted and cooled to 40° C. At 35° C. 7 gm-portions of the composition are poured into slightly chilled suppository molds and allowed to harden therein.

EXAMPLE 8

Hypodermic solution

The solution is compounded from the following ingredients:

| | |
|---|---|
| 11-[4-Methyl-piperazin-(1)-yl]-5H—imidazo[2,1-c][1,4]benzodiazepine | 2.0 parts |
| Sodium chloride | 18.0 parts |
| Distilled water q.s.ad | 2000.0 parts by vol. |

Preparation

The active ingredient and the sodium chloride are dissolved in the distilled water, the solution is filtered to remove any suspended particles, and the filtrate is filled into 2 cc-ampules under aseptic conditions. Finally, the ampules are sterilized and sealed. Each ampule contains 2 mg of the active ingredient.

EXAMPLE 9

Inhalation aerosol

The aerosol is compounded from the following ingredients:

| | |
|---|---|
| 11-[4-Methyl-piperazin-(1)-yl]-5H—imidazo[2,1-c][1,4]benzodiazepine | 1.00 parts |
| Soy bean lecithin | 0.20 parts |
| Propellant gas mixture (Freon 11, 12 and 14) q.s.ad | 100.00 parts |

Preparation

The ingredients are mixed together in conventional manner, and the mixture is filled into aerosol containers equipped with a metering valve which releases between 5 and 20 mg of active ingredient with each actuation.

Any one of the other compounds embraced by formula I or a non-toxic, pharmacologically acceptable acid addition salt thereof may be substituted for the particular active ingredient in Examples 5 through 9. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

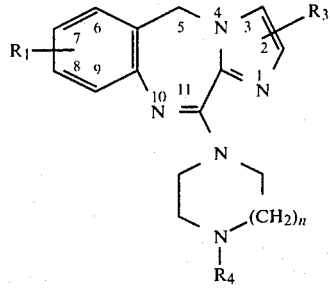

wherein
$R_1$ is hydrogen, fluorine, chlorine, bromine, trifluoromethyl, hydroxyl, amino, methylsulfonamido, alkyl of 1 to 4 carbon atoms, alkoxy of 1 to 3 carbon atoms, (alkyl of 1 to 3 carbon atoms)thio or (alkanoyl of 2 to 4 carbon atoms)amino;
$R_3$ is hydrogen, fluorine, chlorine, bromine or alkyl of 1 to 3 carbon atoms;
$R_4$ is hydrogen, alkyl of 1 to 4 carbon atoms, hydroxy(alkyl of 2 to 4 carbon atoms), (alkoxy of 1 to 2 carbon atoms)-(alkyl of 2 to 4 carbon atoms), alkenyl of 3 to 6 carbon atoms, alkynyl of 3 to 6 carbon atoms, cycloalkyl of 3 to 7 carbon atoms, (cycloalkyl of 3 to 7 carbon atoms)-(alkyl of 1 to 3 carbon atoms) or (unsubstituted or substituted phenyl)-(alkyl of 1 to 3 carbon atoms) where the substituent is fluorine, chlorine, bromine, methyl, methoxy, hydroxyl or trifluoromethyl; and
$n$ is 1 or 2;
or a non-toxic, pharmacologically acceptable acid addition salt thereof.

2. A compound of claim 1, where
$R_1$ is hydrogen, fluorine, chlorine or bromine in the 7- or 8-position;
$R_3$ is hydrogen; and
$R_4$ has the meanings defined in claim 1 or a non-toxic, pharmacologically acceptable acid addition salt thereof.

3. A compound of claim 1, where
$R_1$ is hydrogen, fluorine, chlorine or bromine in the 7- or 8-position;
$R_3$ is hydrogen; and
$R_4$ is hydrogen or methyl;
or a non-toxic, pharmacologically acceptable acid addition salt thereof.

4. The compound of claim 1 which is 11-[4-methyl-piperazin-(1)-yl]-5H-imidazo[2,1-c] [1,4]benzodiazepine.

5. The compound of claim 1 which is 11-[piperazin-(1)-yl]-5H-imidazo[2,1-c] [1,4]benzodiazepine.

6. An antiallergic pharmaceutical composition consisting essentially of an inert pharmaceutical carrier and an effective antiallergic amount of a compound of claim 1.

7. The method of suppressing allergic reactions in a warm-blooded animal in need thereof, which comprises perorally, parenterally, rectally or by inhalation administering to said animal an effective antiallergic amount of a compound of claim 1.

* * * * *